United States Patent
Watanabe et al.

(10) Patent No.: US 7,537,694 B2
(45) Date of Patent: May 26, 2009

(54) METHOD AND DEVICE FOR MULTIDIMENSIONAL LIQUID CHROMATOGRAPHY

(75) Inventors: Masaki Watanabe, Hitachinaka (JP); Shinya Ito, Hitachinaka (JP); Katsuhiro Kanda, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 322 days.

(21) Appl. No.: 11/356,327

(22) Filed: Feb. 17, 2006

(65) Prior Publication Data

US 2006/0219638 A1  Oct. 5, 2006

(30) Foreign Application Priority Data

Mar. 31, 2005  (JP) .............................. 2005-100477

(51) Int. Cl.
 *B01D 15/08* (2006.01)
(52) U.S. Cl. .................... 210/198.2; 210/656; 210/659; 210/143
(58) Field of Classification Search ................ 210/635, 210/656, 659, 143, 198.2; 422/70; 436/161
See application file for complete search history.

(56) References Cited

U.S. PATENT DOCUMENTS

| | | | | |
|---|---|---|---|---|
| 6,942,793 B2 * | 9/2005 | Ito et al. | .................. | 210/198.2 |
| 7,135,111 B2 * | 11/2006 | Deguchi et al. | .......... | 210/198.2 |
| 7,141,161 B2 * | 11/2006 | Ito | ............................. | 210/198.2 |
| 2004/0173509 A1 * | 9/2004 | Ito et al. | ........................ | 210/94 |
| 2004/0178133 A1 * | 9/2004 | Deguchi et al. | .......... | 210/198.2 |
| 2005/0098487 A1 * | 5/2005 | Ito | .............................. | 210/101 |

FOREIGN PATENT DOCUMENTS

| JP | 2004-271272 | 9/2004 |
|---|---|---|
| JP | 2004-271409 | 9/2004 |
| JP | 2005-140659 | 6/2005 |

OTHER PUBLICATIONS

Nagele, E., et al. "Improved 2D Nano-LC/MS for Proteomics Applications: A Comparative Analysis Using Yeast Proteome" Journal of Biomolecular Techniques, Jun. 2004, vol. 15, Is. 2, pp. 134-142.

* cited by examiner

*Primary Examiner*—Ernest G Therkorn
(74) *Attorney, Agent, or Firm*—McDermott Will & Emery LLP

(57) ABSTRACT

In a liquid chromatography, an electrolytic solution starts to be supplied from an injector toward a specimen in a first separating column to transfer components of the specimen from the first separating column toward one of first and second trap columns after a time period more than zero elapses from a time at which another eluting liquid starts to flow through the other one of the first and second trap columns toward a second separating column.

11 Claims, 4 Drawing Sheets

METHOD AND DEVICE FOR MULTIDIMENSIONAL LIQUID CHROMATOGRAPHY

BACKGROUND OF THE INVENTION

The present invention relates to a multidimensional liquid chromatography device including a plurality of separating columns.

In recent years, on a field of proteomics for analyzing exhaustively behaviors of all of various proteins appearing in living bodies, mass spectrographs have been mainly used. The multidimensional liquid chromatography device extracts the various proteins from a specimen obtainable from the living body to be treated by the mass spectrograph.

In the multidimensional liquid chromatography device, columns of respective extracting principles different from each other are connected in series to extract various components from the specimen of the living body. In the multidimensional liquid chromatography device, an eluting solvent used for the extraction in the first column is generally different from an eluting solvent used for the extraction in the second column. On the field of proteomics, an extracting column such as a cation exchanger column or the like in which an electrolytic solution including salt is used as the eluting solvent is used as the first column. Since such solution affects the measurement of the mass spectrograph, an analyzing method is arranged so that a specimen eluted in the first extracting column is temporarily stored in a storing column, and thereafter a flow path switching valve is operated to supply a solution applicable to the mass spectrograph other than the electrolytic solution from the storing column to the second column, whereby the specimen is supplied to the mass spectrograph while the electrolytic solution is prevented from being introduced into the mass spectrograph.

A device including two storing columns (enrichment columns) for storing components of the specimen extracted in the first extracting column (SCX column) at first stage and a flow path switching valve (Micro 10-port valve) for switching the connection between the two storing columns is disclosed by the publication on pages 134-143 by E. Nagele et al. of "Journal of Biomolecular Techniques" of Volume 15, 2004. In this device, the specimen is injected to collect required components of the specimen in the first extracting column, and salt whose concentration is changed is periodically injected into the first extracting column to elute the components of the specimen collected in the first extracting column. The components of the specimen eluted in accordance with the injected salt are stored alternately in the two storing columns. The component of the specimen stored in the storing column connected to the second extracting column (C18 RP column) at second stage through the flow path switching valve is pressed by Nanoflow pump to pass through the second extracting column, and subsequently analyzed.

That is, in the device of the publication, one of the storing columns is connected to the first extracting column to store the component of the specimen eluted from the first extracting column, while the other one of the storing columns is connected to the second extracting column and the Nanoflow pump to elute the component of the specimen from the second extracting column, so that the elution of the component of the specimen from the first eluting column caused by supplying salt can be performed periodically without being stopped.

BRIEF SUMMARY OF THE INVENTION

However, according to the prior art disclosed by the publication, a time at which the elution of the component of the specimen in the first eluting column (the salt injection) is started is substantially simultaneous with a time at which the elution of the component of the specimen in the second eluting column (the liquid transfer by the Nanoflow pump) is started. That is, the extractions at the first and second eluting columns are switched in a common time period, and the component of the specimen to be eluted in the second column was eluted in the first eluting column in the latest eluting step. Therefore, the component of the specimen eluted in the first eluting column and stored in the other one of the storing columns needs to be stored in the other one of the storing columns until next eluting step.

A time period required for the elution in the second eluting column is generally about 1-2 hours, so that the component of the specimen needs to be stored in the storing column for about 1-2 hours. However, the component as protein included by the specimen of the living body and having low interaction with filler in the storing column flows out of the storing column in accordance with time elapse of holding the component in the storing column. Since an important object of the proteomics is to identify infinitesimal protein included by the specimen, an excalation of the component of the specimen during analysis process should be as small as possible.

An object of the present invention is to provide a multidimensional liquid chromatography device in which a component eluted from a first stage column can be effectively introduced into a second stage column.

According to the invention, for example, a multidimensional liquid chromatography device comprises:

an injector for injecting a specimen into an eluting liquid, a first separating column for holding the specimen before and when an electrolytic solution is supplied to the specimen in the first separating column so that components of the specimen are extracted by the electrolytic solution from the specimen in the first separating column, a first pump for feeding the eluting liquid to transfer the specimen from the injector to the first separating column and feeding the electrolytic solution to extract the components of the specimen from the specimen in the first separating column, first and second trap columns each of which is capable of holding the components of the specimen extracted from the specimen in the first separating column, a second pump for feeding another eluting liquid to one of the first and second trap columns after the components of the specimen are held by the one of the first and second trap columns, a second separating column for holding, when at least one of the components of the specimen transferred with the another eluting liquid from the one of the first and second trap columns to the second separating column is eluted by the another eluting liquid from the components thereof in the second separating column, remainder at least one of the components of the specimen, and a detector for detecting the one of the components of the specimen eluted from the components thereof in the second separating column.

Other objects, features and advantages of the invention will become apparent from the following description of the embodiments of the invention taken in conjunction with the accompanying drawings.

DETAILED DESCRIPTION OF THE INVENTION

Figure 1:
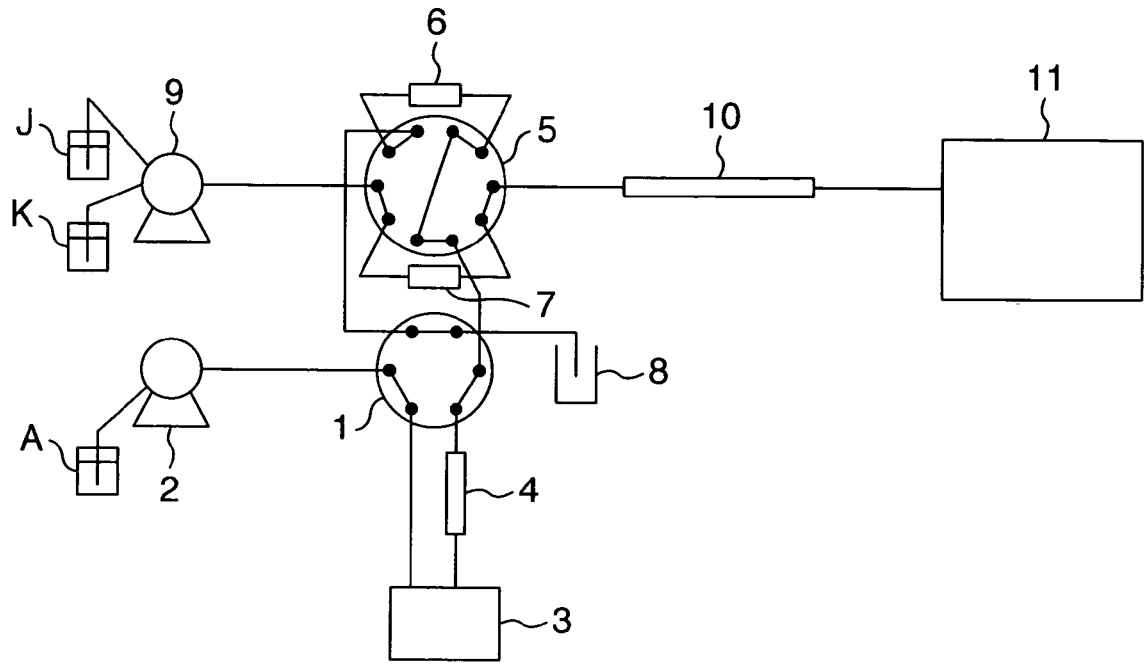
FIG. 1 is a schematic view showing a multidimensional liquid chromatography analysis device of the invention.

Hereafter, an embodiment of the invention is described with making reference to the drawings attached. FIG. 1 is a schematic view showing a multidimensional liquid chromatography device as an embodiment of the invention.

Figure 2:
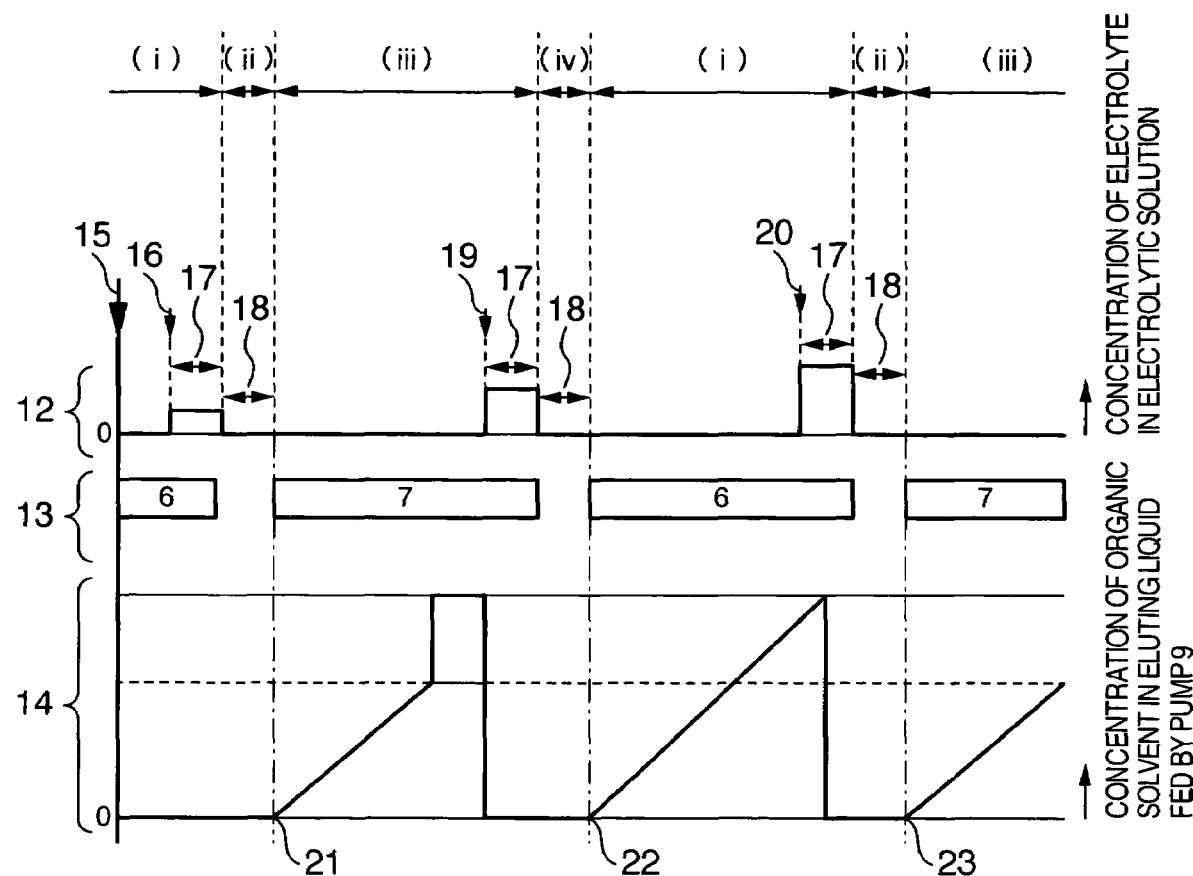
FIG. 2 is a diagram showing an analysis program of the invention.

In FIG. 1, a switching valve 1 changes a flow of a liquid supplied from a pump 2 between a flow path from a specimen injector 3 through an eluting column 4 and a flow path from a ten-ports connection valve 5 through a trap column 6 or 7 to a waste liquid bottle 8. The trap columns 6 and 7 are reverse phase columns. The pump 2 transfers an eluting liquid at a constant flow rate through the flow path selected by the switching valve 1 to the specimen injector 3. The specimen injector 3 includes a container containing therein the specimen and a plurality of the other containers containing therein respective electrolytic (salt or the like) solutions of respective concentrations in gradation. Concentrations of electrolytes in the other containers, a total number of the other containers and amounts of the electrolytic solutions to be injected are changed in accordance with the specimen to be analyzed. After the specimen injector 3 injects the specimen as well as the eluting liquid from the pump 2 into the flow path, the specimen injector 3 injects the electrolytic solutions into the flow path along the predetermined timing on the basis of an analyzing program 12 as shown in FIG. 2 and described below. The specimen injected by the specimen injector 3 is transferred to a first eluting column 4 to be held therein temporarily, and subsequently components of the specimen are eluted by the electrolytic solutions in ascending order of interactions between the first eluting column 4 and the components.

Each of the components eluted in the first eluting column 4 is transferred to the switching valve 1 and the ten-ports connection valves 5 to be stored in the trap column 6 or 7. The ten-ports connection valves 5 selects one of the trap columns 6 and 7 to which each of the components is transferred. The switching valve 1 is connected to a pump 9 and a second eluting column 10 so that the pump 9 supplies eluting liquids J and K to the trap columns while a composition ratio between the eluting liquids J and K is changed along the analyzing program as shown in FIG. 2 and described below. The switching valve 1 changes one of the trap columns to which the liquid is supplied. The components of the specimen in the trap column to which the liquid is supplied from the pump 9 are transferred to the second eluting column 9 so that the components are eluted in the second eluting column 9 to be detected by a detector.

FIG. 2 is a diagram of the analyzing program of the invention. An eluting program in the first eluting column 4 is denoted by 12, an eluting program in the second eluting column 10 is denoted by 14, and one of the trap columns connected to the first eluting column 4 is denoted by 13.

In the eluting program 12, a timing of injecting the specimen from the specimen injector 3 is denoted by 15. Timings of injecting the electrolytic solutions from the specimen injector 3 are denoted by 16, 19 and 20, and the electrolytic solution is supplied during a time period 17 necessary for eluting. A height in the analyzing program 12 corresponds to the concentration of the electrolytic solution, and the concentration is increased stepwise by proceeding of the analyzing program step. Further, the trap column is cleaned during a time period 18 after the time period 17 for eluting.

In the analyzing program 14, times at which the gradient eluting with the eluting liquids K and J by the pump 9 are started are denoted by 21, 22 and 23.

The time at which the electrolytic solution is injected by the specimen injector 3, that is, the time 16 at which the eluting in the first eluting column 4 is started, is set before a time 21 at which the eluting in the second eluting column 10 for required one(s) of the components is started, by (a value not less than) a total amount of a time period 17 necessary for eluting the required one(s) of the components in the first eluting column 4 and a time period 18 necessary for cleaning out the electrolytic solution from the trap column 6 or 7 with a cleaning liquid or solvent A.

The time period 17 necessary for eluting the required one(s) of the components in the first eluting column 4 is a time period sufficient for completing the eluting the required one(s) of the components in the first eluting column 4 from the injection of the electrolytic solution from the specimen injector 3 into the flow path, and may be calculated from a total amount of the injected electrolytic solution and a flow rate thereof by the pump 2.

Figure 3:
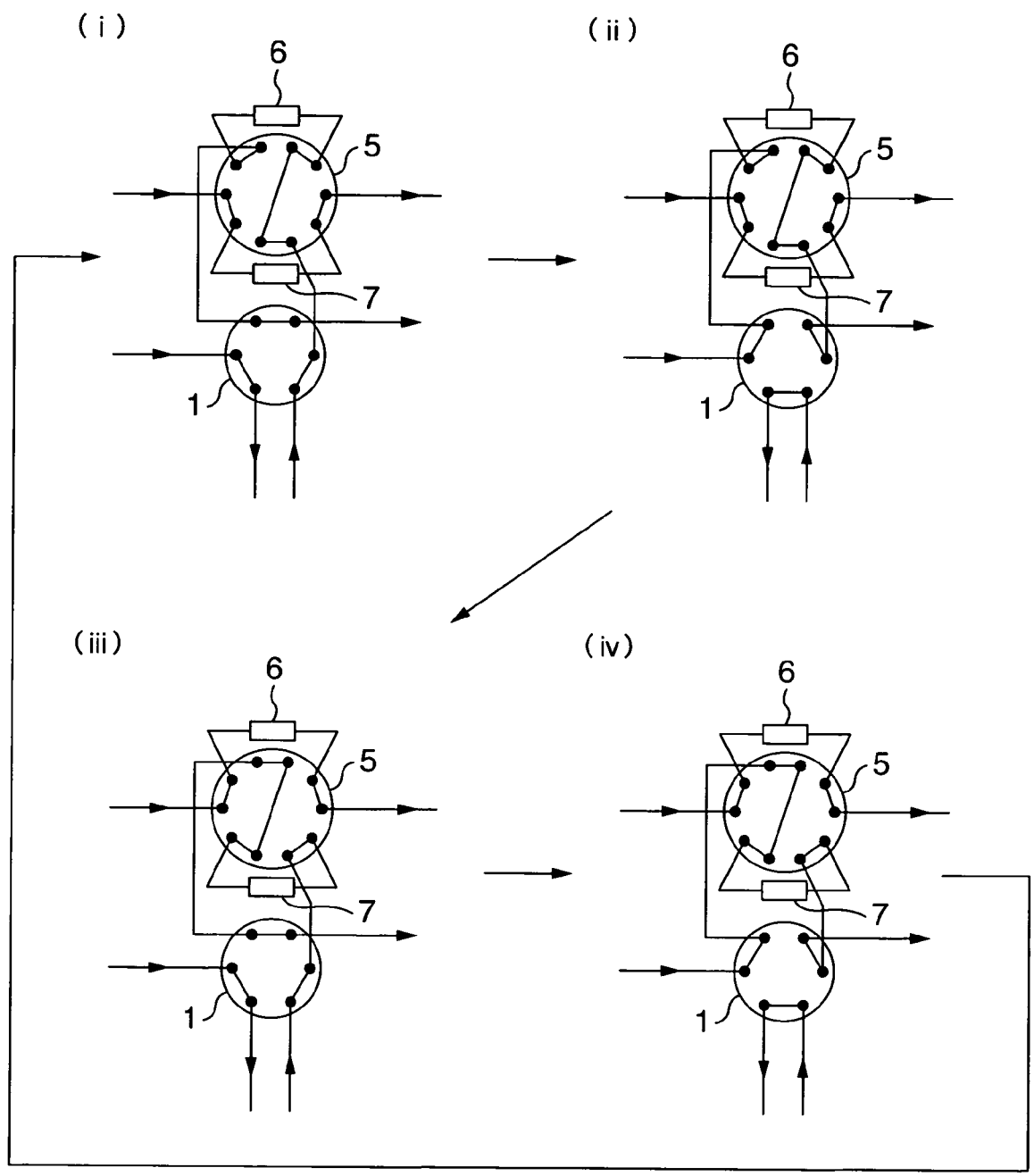
FIG. 3 includes views showing stitching a flow path by a switching valve and a 10-way valve.

FIG. 3 is a schematic view showing flow routes formed by the switching valve 1 and the ten-ports connection valve 5. The flow path is changed among the four routes (i), (ii), (iii) and (iv) in FIG. 3, by the switching valve 1 and the ten-ports connection valve 5.

When the switching valve 1 and the ten-ports connection valve 5 forms the route (i) in FIG. 3, the specimen is injected from the specimen injector 3 so that the required one(s) of the components of the specimen is held by the first eluting column 4. Thereafter, the electrolytic solution is injected from the specimen injector 3 into the first eluting column 4 for the time period 17 necessary for eluting the required one(s) of the components. The required one(s) of the components is eluted from the first eluting column 4 by the electrolytic solution injected into the first eluting column 4, so that the eluted required one(s) of the components is held by the trap column 6. A major part of the eluting liquid not held by the trap column is fed to the waste liquid bottle 8. In this situation, the trap column 7 is connected to the pump 9, the second eluting column 10 and the detector 11 as shown in FIG. 1.

After the time period 17 necessary for eluting the required one(s) of the components from the time 16 at which the eluting in the first eluting column 4 is started has elapsed, the switching valve 1 changes the flow path to the route (ii) in FIG. 3. In this situation, the cleaning liquid A flows into the trap column 6 in a direction opposite to the direction of the route (i) so that the electrolyte is removed from the trap column 6 to be transferred to the waste liquid bottle 8 (Since the trap columns are reverse phase columns to allow the components of the specimen to be adsorbed and prevent the electrolyte from being adsorbed, the electrolyte only exists in the trap column by is not adsorbed therein. Therefore, only the electrolyte can be cleaned out from the trap column by the flow of the cleaning liquid A while the components are held in the trap column). Therefore, the electrolytic solution can be effectively cleaned out from the trap column. Salt is usually used as the electrolyte in the electrolytic solution, but causes a contamination of the detector 11 when being transferred to the detector. Particularly, if the detector 11 is the mass spectroscope, the salt causes the contamination of an ionization source. Further, since the electrolytic solution is higher in ionizing efficiency than the specimen, it deteriorates the ionizing efficiency for the specimen. Therefore, the time period 18 necessary for cleaning out the electrolytic solution enables the detector 11 to be prevented from being contaminated, and the specimen to be detected in high sensitivity.

After the time period 18 necessary for cleaning out the electrolytic solution has elapsed, the switching valve 1 and the ten-ports connection valve 5 changes the flow path to the route (iii) in FIG. 3. In this situation, the trap column 6 is connected to the pump 9, the second eluting column 10 and the detector 11. The pump 9 supplies the eluting liquid J and eluting liquid K to the trap column which the composition ratio therebetween is changed. Whereby, the components of the specimen are transferred from the trap column 6 to the second eluting column 10, and eluted from the second eluting column 10 in ascending order of interactions between the second eluting column 10 and the respective components of the specimen. The eluted components are transferred to the detector 11 as the mass spectrograph to obtain atomic mass numbers of the components.

In the situation shown as the route (iii) in FIG. 3, the trap column 7 is connected to the first eluting column 7 and the waste liquid bottle 8, and filled with the cleaning liquid A. Thereafter, the electrolytic solution of electrolyte concentration higher than the electrolyte concentration of the previously supplied electrolytic solution is injected into the flow path from the specimen injector 3 at a timing 19 which is before a next time 22 at which next time the eluting in the second eluting column 10 for the other required one(s) of the components is started, by (the value not less than) the total amount of the time period 17 necessary for eluting the other required one(s) of the components in the first eluting column 4 and the time period 18 necessary for cleaning out the electrolytic solution from the trap column 7. The other required one(s) of the components eluted from the first eluting column 4 are transferred to the trap column 7 by the electrolytic solution, and held therein. In this situation, the major parts of the cleaning liquid and solution not held by the trap column 7 are transferred to the waste liquid bottle 8.

After the time period 17 necessary for eluting the other required one(s) of the components in the first eluting column 4 has elapsed, the switching valve 1 changed the flow path to the route (iv) shown in FIG. 3. In this situation, the cleaning liquid A is supplied into the trap column 7 in the direction opposite to the direction for the route (iii) shown in FIG. 3 so that the electrolyte is removed from the trap column 7 to the waste liquid bottle 8.

After the time period 18 necessary for cleaning out the electrolytic solution from the trap column 7 has elapsed, the switching valve 1 and the ten-port connection valve 5 changes the flow path to the route (i) shown in FIG. 3, so that the trap column 7 is connected to the pump 9, the second eluting column 10 and the detector 11 to elute from the second eluting column 10 the other required one(s) of the components received by the trap column 7. Further, the trap column 6 receives the further other required one(s) of the components of the specimen.

The switching valve 1 and the ten-port connection valve 5 changes the flow path sequentially in order of (i)→(ii)→(iii)→(iV)→(i)→ . . . in FIG. 3. Incidentally, operations of the pumps 2 and 9, the switching valve 1 and the ten-port connection valve 5 are controlled along the analyzing program shown schematically in FIG. 2 by an operation controller (not shown).

(Example of Analysis)

Hereafter, an example of analysis in which the device shown in FIG. 1 is used, is described.

A cation exchange column (400VHP 8.305 produced by Grace Vaidac inc. (inner diameter 300 μm, length 50 mm, particle diameter 5 μm, pore diameter 900 Å)) was used as the first eluting column 4, a reverse phase column (Picoflit produced by New objective inc. (inner diameter 75 μm, length 50 mm, proteopep IIC18, particle diameter 5 μm)) was used as the second eluting column 10, reverse phase type trap columns (Protecol trap column produced by SGE Inc. (inner diameter 300 μm, length 50 mm, particle diameter 5 μm, pore diameter 300 Å)) were used as the trap columns 6 and 7.

A mixture solution of water 98/acetonitrile 2/formic acid 0.1 (v/v) was used as the cleaning liquid A supplied from the pump 2, a mixture of the cleaning liquid A and 1M ammonium formate was used as the eluting liquid B injected by the specimen injector 3, a solution having the same composition as the cleaning liquid A was used as the eluting liquid J supplied by the pump 9, and a mixture solution of water 2/acetonitrile 98/formic acid 0.1 (v/v) was used as the eluting liquid K supplied by the pump 9. A flow rate of the injected eluting liquid B was 90 μL, a flow rate by the pump 2 was 10 μL/min, a flow rate by the pump 9 was 200 nL/min, and the concentration of the eluting liquid K during the gradient program by the pump 9 was changed from 5% to 65% (from the start of the eluting in the second eluting column 10 to 60 minutes elapse), was kept at 100% (from 60.1 minutes elapse to 80 minutes elapse) and was set at 5% (from 80.1 minutes elapse to 100 minutes elapse).

Figure 4:
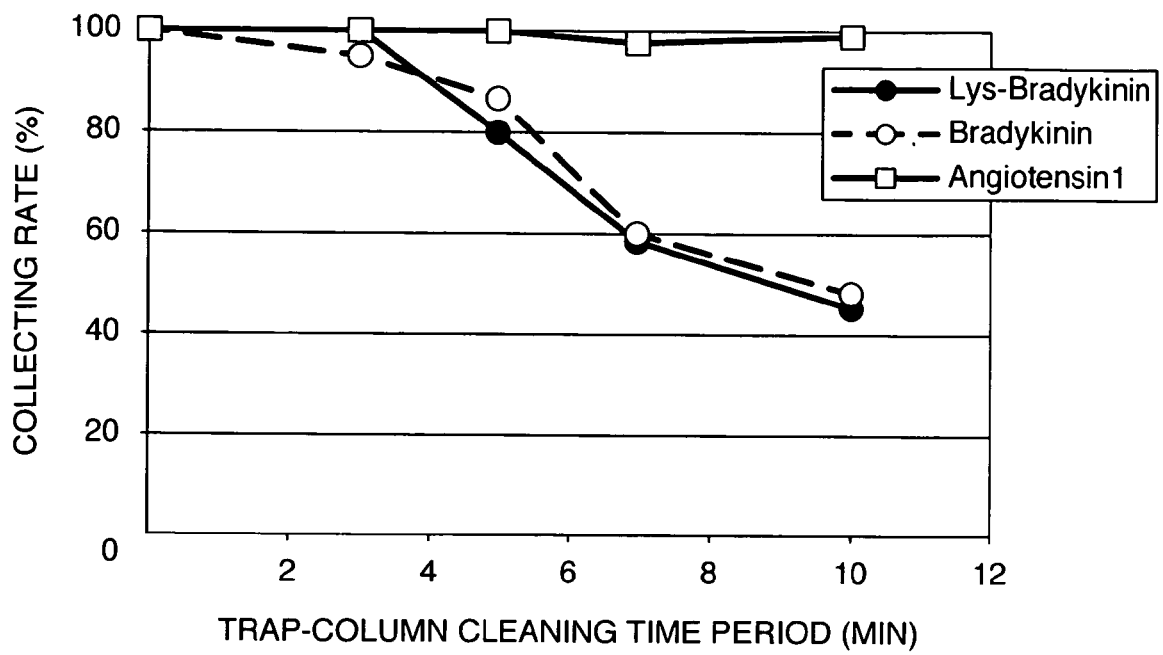
FIG. 4 is a diagram showing a collecting rate of component of specimen obtained when a cleaning time period is changed.

FIG. 4 is a diagram showing a result of efficiency in collecting the components of the specimen obtained when the time period 18 for cleaning out the electrolyte from the trap column was set at each of 0 minute, 3 minutes, 5 minutes, 7 minutes and 10 minutes, and the efficiency was set at 100% when the same amount as an amount of the components collected after the time period 18 of 0 minute elapse was obtained. A peptide mixture solution including angiotensin I, bradykinin and lysyl-bradykinin each concentration of which was 100 fmol/μL was used as the specimen as sample. Under this situation, since the components of not less than 90% were collected within 3 minutes elapse, but the collecting efficiency decreased after 5 minutes elapse, the time period 18 for cleaning out the electrolytic solution from the trap column was set at 3 minutes with taking a balance between the cleaning effect and the collecting efficiency of the components into consideration.

Figure 5:
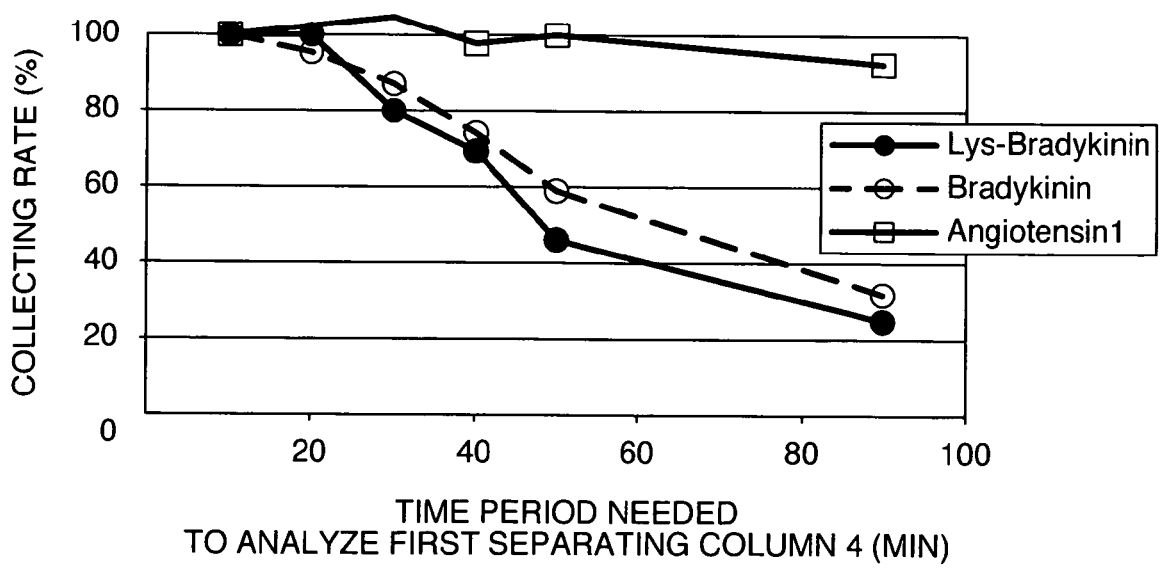
FIG. 5 is a diagram showing the collecting rate of component of specimen obtained when a time period required for analysis is changed.

FIG. 5 is a diagram showing a result of efficiency in collecting each of the above mentioned peptides obtained when the time period 17 for eluting the required one(s) of the components in the first eluting column 4 was set at each of 10 minutes, 20 minutes, 30 minutes, 40 minutes, 50 minutes and 90 minutes, and the efficiency for each of the components was set at 100% when the same amount as an amount of each of the components collected after the time period 17 of 10 minutes elapse was obtained. As understandable from this result, the collecting efficiency for each of the peptides was not less than 90% when the time period 17 for eluting the required one(s) of the components in the first eluting column 4 was not more than 20 minutes, the collecting efficiency for each of bradykinin and lysyl-bradykinin whose interaction with the trap column is small decreased in accordance with an increase of the time period 17, and the collecting efficiency for each of bradykinin and lysyl-bradykinin decreased to about 30% when the time period 17 of 90 minutes elapsed. That is, the shorter a time period during which the components of the specimen eluted from the first eluting column 4 is contained by the trap column is, the higher the collecting efficiency is.

According to the invention, the time at which the eluting in the first eluting column 4 is started is set before the time at which the subsequent eluting in the second eluting column 10 is started, by (a value not less than) a total amount of the time period 17 necessary for eluting the required one(s) of the components in the first eluting column 4 and the time period 18 necessary for cleaning out the electrolytic solution from the trap column 6 or 7, so that a time period between the time at which the eluting in the first eluting column 4 is started and the time at which the subsequent eluting in the second eluting column 10 is started can be decreased to increase sensitivity in detection of the multidimensional liquid chromatography device.

Figure 6:
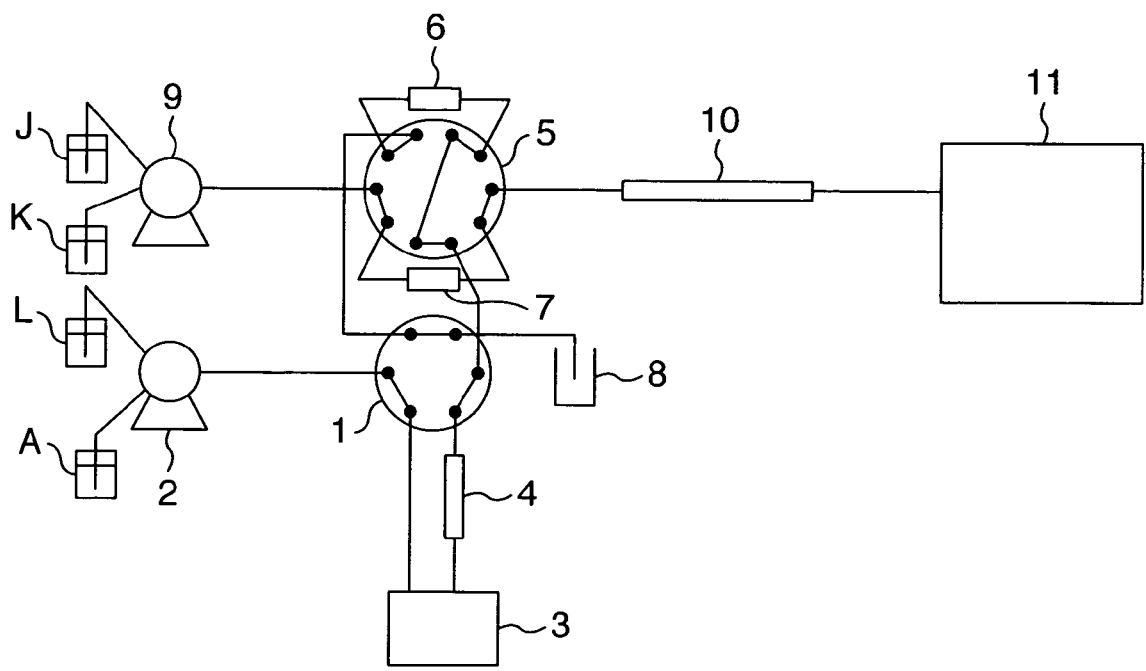
FIG. 6 is a schematic view showing another multidimensional liquid chromatography analysis device of the invention.

In the embodiment as shown in FIG. 1, the electrolytic solution injected from the injector 3 is fed with the eluting liquid urged by the pump 2, that is, the electrolytic solution is indirectly fed by the pump 2. However, as shown in FIG. 6, the electrolytic solution as well as the eluting liquid may be supplied to an upstream side of the pump 2 to be directly fed by the pump 2.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A liquid chromatography device comprising:
a source of electrolytic solution,
an injector for injecting a specimen into an eluting liquid,
a first separating column for holding the specimen before and when an electrolytic solution is supplied to the specimen in the first separating column so that components of the specimen are extracted by the electrolytic solution from the specimen in the first separating column,
a first pump for feeding the eluting liquid to transfer the specimen from the injector to the first separating column and feeding the electrolytic solution to extract the components of the specimen from the specimen in the first separating column,
first and second trap columns each of which is capable of holding the components of the specimen extracted from the specimen in the first separating column,
a second pump for feeding another eluting liquid to one of the first and second trap columns after the components of the specimen are held by the one of the first and second trap columns,
a second separating column for holding, when at least one of the components of the specimen transferred with the another eluting liquid from the one of the first and second trap columns to the second separating column is eluted by the another eluting liquid from the components thereof in the second separating column, remainder at least one of the components of the specimen,
a detector for detecting the at least one of the components of the specimen eluted from the components thereof in the second separating column, and
an operation controller for controlling said first and second pumps, wherein:
the operation controller is configured to control operations of the first and second pumps so that
when said second pump feeds said another eluting liquid from the one of the first and second trap columns to the second separating column before said second pump feeds said another eluting liquid from the other one of the first and second trap columns to the second separating column,
the second pump changes a concentration of an organic solvent included by the another eluting liquid from first concentration for extracting the at least one of the components from the components of the specimen in the second separating column to second concentration, and
keeps the second concentration lower than the first concentration with the first pump feeding the eluting liquid from the first pump through the other one of the first and second trap columns while preventing the eluting liquid from flowing through the first separating column.

2. A liquid chromatography device according to claim 1, wherein the said operation controller is configured to control the second pump to keep said second concentration at zero.

3. A liquid chromatography device comprising:
a source of electrolytic solution,
an injector for injecting a specimen into an eluting liquid,
a first separating column for holding the specimen before and when an electrolytic solution is supplied to the specimen in the first separating column so that components of the specimen are extracted by the electrolytic solution from the specimen in the first separating column,
a first pump for feeding the eluting liquid to transfer the specimen from the injector to the first separating column and feeding the electrolytic solution to extract the components of the specimen from the specimen in the first separating column,
first and second trap columns each of which is capable of holding the components of the specimen extracted from the specimen in the first separating column,
a second pump for feeding another eluting liquid to one of the first and second trap columns after the components of the specimen are held by the one of the first and second trap columns,
a second separating column for holding, when at least one of the components of the specimen transferred with the another eluting liquid from the one of the first and second trap columns to the second separating column is eluted by the another eluting liquid from the components thereof in the second separating column, remainder at least one of the components of the specimen,
a detector for detecting the at least one of the components of the specimen eluted from the components thereof in the second separating column, and
an operation controller for controlling said first and second pumps and said injector,
wherein said operation controller is configured to control the injector and the second pump so that a time period from a time at which a supply of the electrolytic solution from the injector to the specimen in the first separating column for transferring the components of the specimen from the first separating column to the one of the first and second trap columns is finished to a subsequent time at which the another eluting liquid starts to flow from the second pump through the one of the first and second trap columns toward the second separating column is less than another time period from a time at which the another eluting liquid starts to flow from the second pump through the other one of the first and second trap columns toward the second separating column to a subsequent time at which the supply of the electrolytic solution from the injector toward the specimen in the first separating column for transferring the components of the specimen from the first separating column to the one of the first and second trap columns is started.

4. A liquid chromatography device comprising:

a source of electrolytic solution, an injector for injecting a specimen into an eluting liquid, a first separating column for holding the specimen before and when an electrolytic solution is supplied to the specimen in the first separating column so that components of the specimen are extracted by the electrolytic solution from the specimen in the first separating column, a first pump for feeding the eluting liquid to transfer the specimen from the injector to the first separating column and feeding the electrolytic solution to extract the components of the specimen from the specimen in the first separating column, first and second trap columns each of which is capable of holding the components of the specimen extracted from the specimen in the first separating column, a second pump for feeding another eluting liquid to one of the first and second trap columns after the components of the specimen are held by the one of the first and second trap columns, a second separating column for holding, when at least one of the components of the specimen transferred with the another eluting liquid from the one of the first and second trap columns to the second separating column is eluted by the another eluting liquid from the components thereof in the second separating column, remainder at least one of the components of the specimen, a detector for detecting the at least one of the components of the specimen eluted from the components thereof in the second separating column, , and an operation controller for controlling said first and second pumps and the injector, wherein:

said operation controller is configured to control the first and second pumps and the injector so that a time period from a time at which a flow of the eluting liquid from the first pump through the one of the first and second trap columns while preventing the eluting liquid from flowing through the first separating column is finished to a subsequent time at which the another eluting liquid starts to flow from the second pump through the one of the first and second trap columns toward the second separating column is less than another time period from a time at which the another eluting liquid starts to flow from the second pump through the other one of the first and second trap columns toward the second separating column to a subsequent time at which a supply of the electrolytic solution from the injector toward the specimen in the first separating column for transferring the components of the specimen from the first separating column to the one of the first and second trap columns is started.

5. A liquid chromatography device comprising:

a source of electrolytic solution, an injector for injecting a specimen having components, wherein said specimen is injected into an eluting liquid, a first separating column for holding the specimen before and when an electrolytic solution is supplied to the specimen in the first separating column so that components of the specimen are extracted by the electrolytic solution from the specimen in the first separating column, a first pump for feeding the eluting liquid to transfer the specimen from the injector to the first separating column and feeding the electrolytic solution to extract the components of the specimen from the specimen in the first separating column, first and second trap columns each of which is capable of holding the components of the specimen extracted from the specimen in the first separating column, a second pump for feeding another eluting liquid to one of the first and second trap columns after the components of the specimen are held by the one of the first and second trap columns, a second separating column for holding, when at least one of the components of the specimen transferred with the another eluting liquid from the one of the first and second trap columns to the second separating column is eluted by the another eluting liquid from the components thereof in the second separating column, remainder at least one of the components of the specimen, a detector for detecting the at least one of the components of the specimen eluted from the components thereof in the second separating column, ,and an operation controller for controlling said first and second pumps and the injector, wherein:

the operation controller is configured to control the injector to start the supply of the electrolytic solution toward the specimen in the first separating column to transfer the components of the specimen from the first separating column toward the one of the first and second trap columns after a time period more than zero elapses from a time at which the another eluting liquid starts to flow from the second pump through the other one of the first and second trap columns toward the second separating column.

6. A multidimensional liquid chromatography device according to claim 5, wherein:

said operation controller is configured to control the injector so that the time period is less than another time period from the time to a subsequent time at which the another eluting liquid starts to flow from the second pump through the one of the first and second trap columns toward the second separating column.

7. A liquid chromatography device according to claim 5, wherein the one of the components of the specimen is capable of being detected by the detector during the time period from the time.

8. A liquid chromatography device according to claim 5, wherein:

said operation controller is configured to control the injector so that the time period is not less than another time period during which the electrolytic solution flows from the injector through the first separating column toward the one of the first and second trap columns.

9. A liquid chromatography device according to claim 5, wherein:

said operation controller is configured to control the injector so that the time period is not less than another time period during which the eluting liquid flows from the first pump through the one of the first and second trap columns while preventing the eluting liquid from flowing through the first separating column.

10. A liquid chromatography device according to claim 5, wherein:

said operation controller is configured to control the injector so that the time period is not less than another time period during which the electrolytic solution flows from the injector through the first separating column toward the one of the first and second trap columns, and subsequently the eluting liquid flows from the first pump through the one of the first and second trap columns while preventing the eluting liquid from flowing through the first separating column.

11. A liquid chromatography device according to claim 5, wherein:

said operation controller is configured to control the injector so that the time period is not less than another time period during which the specimen flows with the eluting liquid from the injector toward the first separating column.

\* \* \* \* \*